(12) United States Patent
Tararuj et al.

(10) Patent No.: US 6,403,186 B1
(45) Date of Patent: Jun. 11, 2002

(54) PRODUCT SAMPLER

(75) Inventors: Christopher Tararuj, Hamilton; Patrick Donahue, Belle Mead; Robert E. Katz, Short Hills; David DeSchryver, East Brunswick; Robert Weiser, Sea Bright, all of NJ (US)

(73) Assignee: AKI, Inc., New York, NY (US)

( * ) Notice: Subject to any disclaimer, the term of this patent is extended or adjusted under 35 U.S.C. 154(b) by 0 days.

(21) Appl. No.: 09/345,911

(22) Filed: Jul. 1, 1999

Related U.S. Application Data
(60) Provisional application No. 60/074,262, filed on Feb. 10, 1998.

(51) Int. Cl.[7] .............................. A61L 9/012; B32B 9/00
(52) U.S. Cl. ........................ 428/40.1; 239/34; 239/53; 239/54; 239/60; 424/76.4; 424/486; 428/40.2; 428/130; 428/195
(58) Field of Search ................................ 428/40.1, 130, 428/195, 40.2; 424/486, 76.4; 239/34, 53, 54, 60

(56) References Cited

U.S. PATENT DOCUMENTS

| | | | |
|---|---|---|---|
| 3,494,505 A | 2/1970 | Huebner et al. | |
| 3,685,734 A | 8/1972 | Paciorek et al. | |
| 3,888,689 A | 6/1975 | Maekawa et al. | |
| 4,606,956 A | 8/1986 | Charbonneau et al. | |
| 4,769,264 A | 9/1988 | Dreger | |
| 4,874,129 A | 10/1989 | DiSapio et al. | |
| 4,876,136 A | 10/1989 | Chang et al. | 428/130 |
| 4,880,690 A | 11/1989 | Szycher et al. | |
| 4,889,755 A | 12/1989 | Charbonneau | 428/40.2 |
| 4,890,872 A | 1/1990 | Parrotta et al. | 283/56 |
| 4,906,488 A | 3/1990 | Pera | 426/573 |
| 4,908,252 A | 3/1990 | Carnahan et al. | 428/87 |
| 4,923,063 A | 5/1990 | Tararuj | 206/484 |
| 4,925,667 A | 5/1990 | Fellows et al. | 424/401 |
| 4,940,584 A | 7/1990 | Tararuj | 424/401 |
| 4,952,400 A | 8/1990 | Tararuj et al. | 424/401 |
| 4,988,557 A | 1/1991 | Charbonneau | 428/204 |
| 4,990,381 A | 2/1991 | Holzner | 428/35.3 |
| 5,018,974 A | 5/1991 | Carnahan et al. | 434/98 |
| 5,050,910 A | 9/1991 | Schechter et al. | 283/105 |

(List continued on next page.)

FOREIGN PATENT DOCUMENTS

| | | |
|---|---|---|
| CA | 2073922 | 1/1993 |
| WO | WO88/03374 | 5/1988 |
| WO | WO92/14607 | 9/1992 |
| WO | WO94/05182 | 3/1994 |
| WO | WO95/33619 | 12/1995 |
| WO | WO98/10917 | 3/1998 |

*Primary Examiner*—Nasser Ahmad
(74) *Attorney, Agent, or Firm*—Law Offices of Mitchell P. Novick; Benjamin Appelbaum (57) ABSTRACT

A product sampler including a substrate layer, a barrier layer covering the substrate layer, a gelatinoid product layer covering and in contact with the barrier layer, and a barrier layer covering and in contact with the product layer is provided. The gelatinoid product layer may include a microencapsulated product, such as a fragrance. In preferred embodiments of the invention, the gelatinoid product layer includes a microencapsulated fragrance carried in a gelatinoid liquid vehicle, which vehicle may comprise, for example, propylene glycol, polyethylene glycols, glycerin, or mixtures thereof. In a highly preferred embodiment of the invention, the product sampler is in the form of a magazine insert having a protruding trimmable non-barrier substrate tab portion, whereby a user may remove a trim portion from the trimmable edge portion after binding the insert into a magazine without removing barrier material with the removed trim portion. Also disclosed is a product sampler in the form of a label.

5 Claims, 4 Drawing Sheets

U.S. PATENT DOCUMENTS

| | | |
|---|---|---|
| 5,051,305 A | 9/1991 | Whitaker, Sr. ............ 428/402.2 |
| 5,093,182 A | 3/1992 | Ross ........................... 428/195 |
| 5,161,688 A | 11/1992 | Muchin ...................... 206/484 |
| 5,242,521 A | 9/1993 | Hibsch et al. .............. 156/200 |
| 5,248,537 A | 9/1993 | Giannovola |
| 5,268,214 A | 12/1993 | Charbonneau |
| 5,341,992 A | 8/1994 | Bishopp ...................... 239/34 |
| 5,389,174 A | 2/1995 | Hibsch et al. |
| 5,391,374 A | 2/1995 | Charbonneau .............. 428/401 |
| 5,391,420 A | 2/1995 | Bootman et al. |
| 5,395,047 A | 3/1995 | Pendergrass, Jr. |
| 5,419,958 A | 5/1995 | Charbonneau |
| 5,439,172 A | 8/1995 | Comyn et al. ................ 239/34 |
| 5,445,821 A | 8/1995 | Brown et al. ................ 424/401 |
| 5,534,105 A | 7/1996 | Boyd |
| 5,566,693 A | 10/1996 | Gunderman et al. |
| 5,609,710 A | 3/1997 | Charbonneau |
| 5,611,972 A | 3/1997 | Tararuj et al. ................ 264/4.1 |
| 5,622,263 A | 4/1997 | Greenland |
| 5,637,401 A * | 6/1997 | Berman et al. .......... 252/315.2 |
| 5,645,161 A | 7/1997 | Whitaker et al. |
| 5,715,849 A * | 2/1998 | Vanbraekel .................. 132/314 |
| 5,799,675 A | 9/1998 | Gunderman et al. |
| 5,885,701 A | 3/1999 | Berman et al. |
| 5,918,908 A | 7/1999 | Barnett et al. |
| 5,928,748 A | 7/1999 | Jones et al. |
| 5,953,885 A | 9/1999 | Berman et al. |
| 5,992,889 A | 11/1999 | Barnett et al. |
| 6,006,916 A | 12/1999 | Matsos et al. |
| 6,125,614 A | 10/2000 | Jones et al. |
| 6,182,420 B1 | 2/2001 | Berman et al. |
| 6,187,432 B1 | 2/2001 | Krish et al. |
| 6,190,730 B1 | 2/2001 | Matsos et al. |

* cited by examiner

PRODUCT SAMPLER

This application claims priority to prior provisional application Serial No. 60/074,262, filed Feb. 10, 1998, the content of which is hereby incorporated by reference in its entirety.

TECHNICAL FIELD OF THE INVENTION

The invention relates generally to a product sampler, and more particularly to a product sampler that is capable of being provided in the form of a handout, mailer, label, or bindable magazine insert.

BACKGROUND OF THE INVENTION

The prior art has provided numerous sampler devices for use in connection with promotion of the sale of fragrances and other products. Known samplers typically are inserted into magazines and catalogs, are used as statement enclosures, or are handed out individually by salespersons at retail establishments. Such samplers typically are of a non-laminar construction and comprise one sheet of a substrate, such as paper, which sheet is temporarily bonded to itself with an adhesive. A microencapsulated fragrance oil is disposed within the adhesive, such that the adhesive thus both bonds the microcapsules to the substrate sheet and binds together the interior faces of the substrate sheet. When a user separates the sheets, some or all of the microcapsules rupture, thereby releasing the fragrance contained therein for evaluation by the user. A layer of a barrier material, such as a plastic or metal foil, may be utilized to overwrap the sampler to prevent leakage of the fragrance from the sampler.

One long-standing problem associated with known samplers is their tendency to leak, that is, to prematurely emit the fragrance intended to be delivered at a later time by the sampler. This problem is known as the "preodor" problem. Preodor is particularly troublesome for product samplers that are provided as magazine inserts. Typically, such product samplers will be provided in the form of a paper insert bound directly into the magazine. During the manufacture, application, cutting and binding of the insert, some of the microcapsules within the sampler can rupture, thus causing premature release of the fragrance. Such premature leakage of the fragrance can render the sampler less effective in delivering a suitable dose of fragrance to the end user. Moreover, postal regulations place limits on the levels of emissions of fragrance from magazines and other articles that are sent through the mails. Thus, if rules become further restrictive, magazine publishers may be required to take special and expensive measures to prevent leakage of fragrance from the insert, such as wrapping the entire magazine with a barrier film material.

In recognition of these problems, the art has provided label or pouch products that are designed to effectively address the preodor issues. These products do not utilize a microencapsulated fragrance oil. Instead, the fragrance is provided in the form of a volatile oil carried in a volatile carrier to provide a "wearable" product that a consumer can apply to the skin. Such label or pouch products rely on a barrier film and an adhesive perimeter seal to contain the volatile fragrance oil and volatile vehicle contained therein. While the use of such a perimeter seal may be advantageous in some cases, such products generally are costly to produce. Moreover, the label or pouch generally must be secured to a separate substrate before the label or pouch may be used as a magazine insert or handout, and thus additional costly handling is generally required.

Another problem in the art relates to the binding of magazines containing product samplers. Magazine binderies sometimes need to cut off a portion of the insert after it is bound into the magazine, a step known as "taking a trim." Such a step is often necessary to properly size or position the insert within the magazine. Because of the need to take a trim, it can be difficult and costly to utilize samplers that are of a laminar construction composed of plural layers of discrete materials. If a product sampler were to comprise a laminate of a substrate and a barrier material, for example, a trim portion taken from the sampler would comprise a laminate of the barrier material and the substrate material. The removed barrier film in the trim portion would be difficult to separate from the paper, and thus the trim portion would be difficult to recycle and consequently more costly to dispose of. For this reason, such laminar products are not generally accepted at binderies.

Another problem with known samplers is that their utility generally is limited to the delivery of microencapsulated products. Such samplers generally are not cost effective for delivery of other products, such as cosmetics, and particularly not products such as wet or oil-based products or color cosmetics such as lipsticks, rouges, blushes, foundations, and the like.

In light of the foregoing problems with known samplers, there exists a need in the art for an inexpensive fragrance product sampler that will not prematurely emit the fragrance contained therein. A need exists for an economical fragrance sample capable of delivering a product that can be applied to the skin. A further need exists for a sampler that will maintain the integrity of other products, in particular wet or oil-based products contained in the sampler. Ideally, the sampler should be of simple construction, such that it may be manufactured quickly and inexpensively. The sampler further should be susceptible to processing and handling without difficulty. A need further exists for a sampler having a non-barrier trimmable substrate edge, such that a bindery may take a trim portion from the sampler without removing barrier material with the removed trim portion.

OBJECTS AND SUMMARY OF THE INVENTION

It is a general object of the invention to provide a sampler for fragrances and other products, the sampler having sufficient barrier properties so as to prevent or substantially inhibit the emission of volatile components such as odor components from the sampler.

Another object is to provide a sampler that is suitable for delivering products other than microencapsulated products, such products including, for example, color cosmetic products. In keeping with this object, the integrity of the product carried by the sampler should not be compromised by incorporation or absorption of the product or any components thereof into the sampler substrate, such that a true product representation of color, feel, texture, and/or fragrance can be achieved by preventing migration of non-volatile components into the substrate.

Another general object of the invention is to provide a sampler having a non-barrier trimmable edge, whereby a bindery may remove a trim portion from the sampler without removing barrier material with the removed trim portion.

Another object is to provide a sampler that retains the facility of opening of a conventional paper sampler but that has the capability to deliver a usable liquid sample, and that further has the advantage of being reclosable so as not to leave an unsightly flap or label.

It is a further object of the invention to emulsify and stabilize a fragrance oil in a non-volatile vehicle.

These objects have been achieved in one or more embodiments of the present invention. In accordance with one embodiment of the invention, the invention provides a product sampler that includes a substrate layer, a barrier layer covering the substrate layer, a gelatinoid product layer in contact with and covering the barrier layer, and a barrier layer in contact with and covering the product layer. The gelatinoid product layer may be applied to the barrier layer without a separate adhesive layer, and may include a microencapsulated product, such as a fragrance. Alternatively, the gelatinoid product layer may include or comprise a product that is not microencapsulated. A user may expose the gelatinoid product layer by removing the covering barrier layer to expose the gelatinoid product layer, and may thereby sample the product. A repositionable adhesive may be used to allow for reclosability of the sampler. In typical use, the user will remove only a portion of the product in the gelatinoid product layer upon each use of the sampler, thus allowing for plural uses of the sampler.

The use of a gelatinoid product layer in conjunction with the sampler provides for numerous advantages. For example, the gelatinoid nature of the product layer allows for a pleasing skin feel. Because the product layer is disposed on the barrier layer, and is not adhesively secured to the substrate layer, the sampler is suitable for delivering not only fragrance products, but also cosmetic products and other products. The barrier layer may be placed on an interior surface of the substrate, and in contact with the product layer, thus achieving an effective barrier function without the need to connect the product layer to the substrate with a separate adhesive.

In accordance with another embodiment of the invention, a method for preparing a sampler is provided. The method includes the steps of providing a substrate and placing a barrier layer over a portion of the substrate to define plural substrate regions including a barrier substrate region and a non-barrier substrate region, and removing a portion of the barrier substrate region to leave a trimmable substrate edge portion. When a sampler is prepared according to the present inventive method, a trim portion may be removed from the sampler without also removing the barrier material from the sampler.

In accordance with yet another embodiment of the invention, a product sampler in the form of a label is provided. The label includes two layers of a substrate barrier material containing therebetween a gelatinoid product layer. Because the substrate material itself possesses barrier properties, no separate barrier material is required.

DESCRIPTION OF THE INVENTION

The sampler of the invention preferably takes the form of a bindable magazine insert. Generally, the insert of the invention comprises a laminate of a substrate material and a barrier material, and further includes a product layer disposed within layers of the barrier material. The substrate and barrier may be made of known or conventional materials and assembled in a conventional manner.

For example, with respect to the substrate, numerous suitable materials are known in the art. Typical samplers include paper substrates, and the sampler of the invention may so include a paper-substrate. The paper may be of a grade similar to that used in conventional product samplers. However, while known samplers typically require expensive grades of paper, the unique construction of the product sampler of the present invention allows for the use of any paper substrate to be employed in conjunction with the invention. Thus, lower grades of paper may be employed in conjunction with the invention. Moreover, in conjunction with the preparation of conventional samplers, some higher grades of paper, such as whiter or brighter paper than is conventionally used, are not acceptable because such papers may be incompatible with microencapsulated fragrances. In contrast, in conjunction with the present invention, such higher grades of paper may be employed. More generally, any web or sheet of material useful as a substrate may be employed in conjunction with the invention. For example, the substrate may be a polymeric film of material, such as a polypropylene film or a polyester film. One suitable film is sold by the duPont Corporation under the trademark MYLAR. If a polymeric film is used as a substrate, the barrier properties of the film may be adequate to protect the integrity of the sampler, and no separate barrier material need be employed.

The sampler generally further includes a barrier material, which material may be any material that prevents release of desirable components from the product layer. For example, when the product layer includes a microencapsulated fragrance dispensed in a gelatinoid product vehicle, the barrier layer should be a material that prevents migration of non-volatile components of the product layer into and through the substrate. The barrier layer thus should be a material which inhibits release of fragrance and other volatile materials.

Of the numerous suitable materials known in the art, preferred barrier materials include metal foils, polymeric films, such as polypropylene, polyethylene, polyester and polyvinylidinedichloride, and coextruded or laminar films, such as a polyethylene/polyamide/polyethylene film. The product layer may be applied onto the barrier layer by conventional methods, such as, for example, spray coating, silk screening, extrusion, flexography, letterpress application, and so forth. The invention is not limited to the foregoing barrier materials or application methods, and it is contemplated that other polymeric or metallic films or other films or combinations could be employed in conjunction with the invention.

Figure 1:
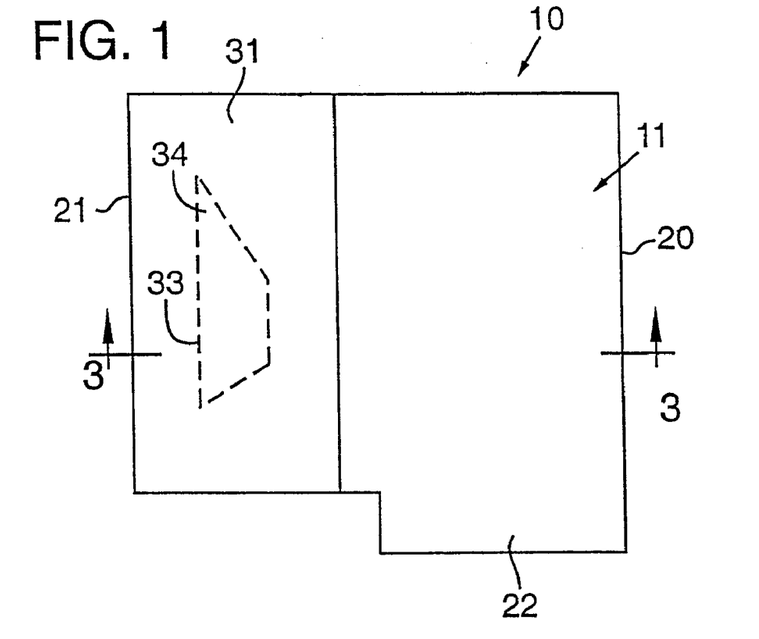
FIG. 1 is a plan view of one embodiment of the sampler of the invention, showing the sampler in a closed position.
Figure 2:
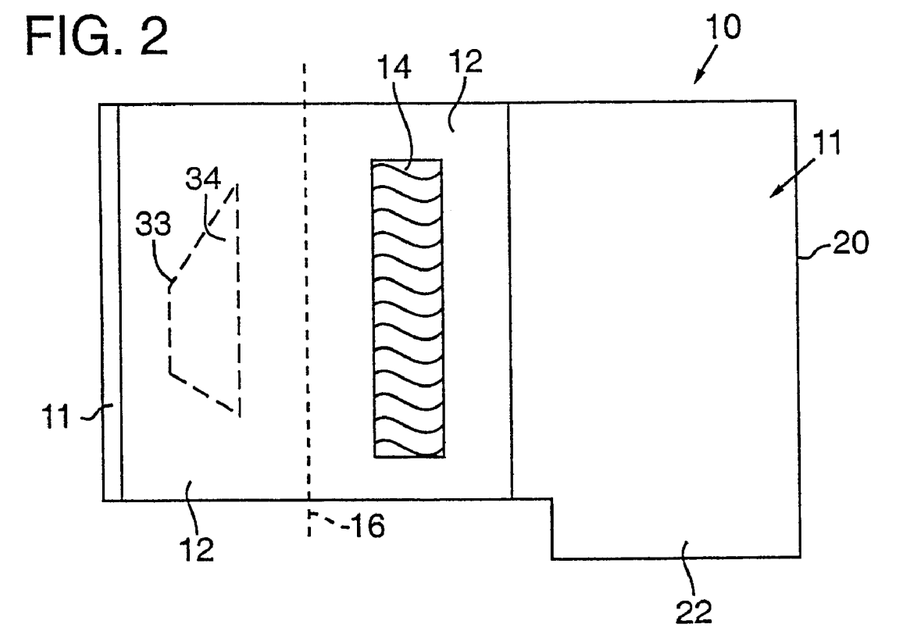
FIG. 2 is a plan view of the sampler shown in FIG. 1, shown in an open position with the product layer exposed.
Figure 3:
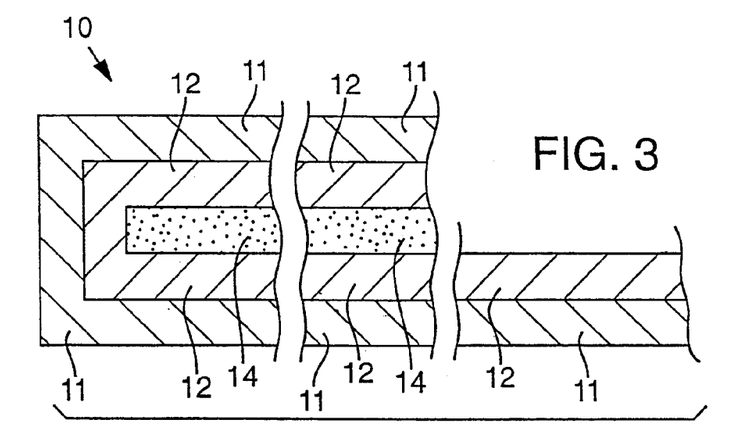
FIG. 3 is an enlarged partial cross-sectional view taken along line 3—3 in FIG. 1.
Figure 5:
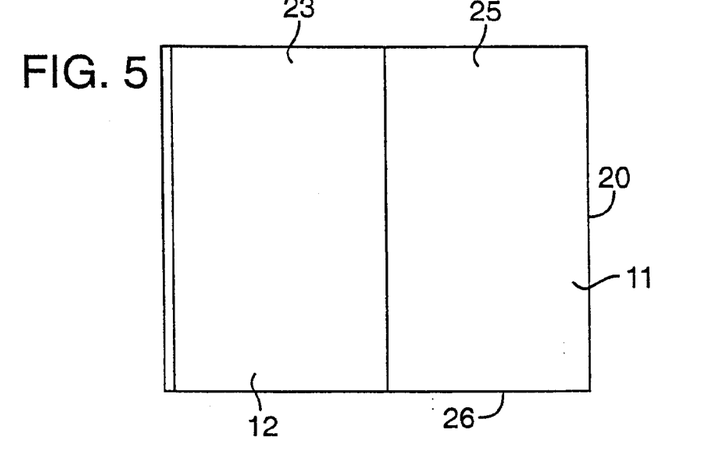
FIG. 5 is a plan view of an intermediate prepared during the manufacturing of the sampler shown in FIG. 1.
Figure 7:
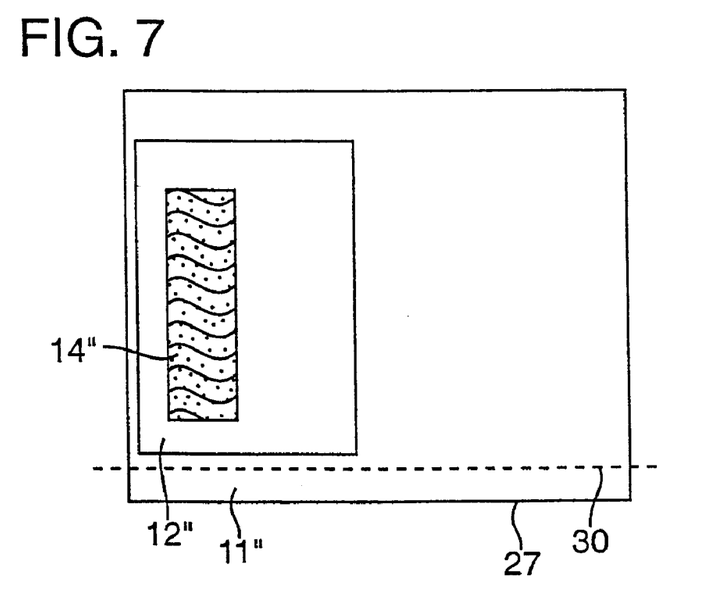
FIG. 7 is a plan view of another embodiment of the sampler of the invention, shown in an open position with the product exposed, the sampler constructed with a discontinuous application of the barrier film to the substrate and further including an alternative placement of the product layer.

Referring now to FIGS. 1–3, the sampler 10 is of laminar construction and includes a substrate 11 having a layer of barrier material 12 (shown in. FIGS. 2–3) integrally bonded to at least a portion thereof, and preferably bonded only to a portion thereof when the sampler takes the form of a magazine insert. The sampler may be made by applying the barrier film material in a continuous strip over the substrate material to form a laminar intermediate structure, as shown in FIG. 5. Alternatively, the barrier film material may be applied discontinuously over the substrate to form an intermediate structure, as shown in FIG. 7 with respect to substrate 11" and barrier material 12".

The sampler further includes a product, and, as set forth in more detail hereinbelow, most preferably includes a gelatinoid product. In the preferred embodiment shown in FIGS. 2–3, a gelatinoid product layer 14 is placed on at least a portion of the barrier layer, and one portion of the sampler is folded along fold line 16 (shown in FIG. 2) to seal the product layer 14 between folded portions of the barrier layer 12, as best shown in FIG. 3. It is contemplated that plural product layers of different fragrances or products arranged adjacent or proximate to one another on the barrier layer. For example, the sampler may be used to provide samples of two or more complementary fragrances, such as "his and her" fragrances. The product layer or layers may be applied to the barrier layer in any suitable manner, for example, by employing conventional manufacturing methods.

Figure 4:
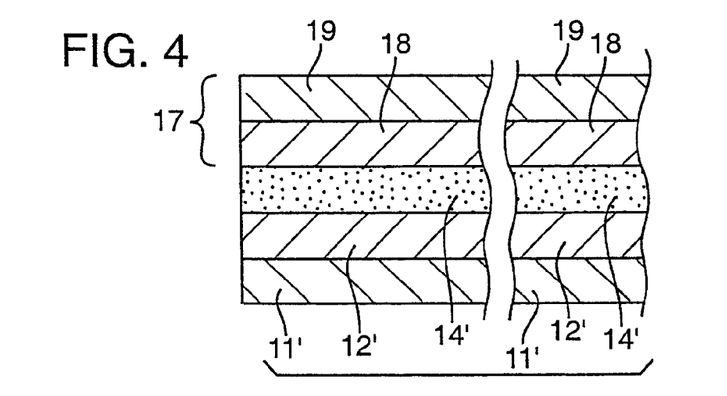
FIG. 4 is an enlarged partial cross-sectional view of another embodiment of the sampler of the invention.

An alternative construction for the sampler is shown in FIG. 4. In this embodiment, a separate covering laminar ribbon 17 that is composed of barrier layer 18 and substrate material 19 are applied over the product layer 14', barrier layer 12', and substrate layer 11' to thereby seal the product layer 14' within the sheets of barrier material 12', 18. The material of the barrier layer 18 of the laminar ribbon 17 may be the same or different material as in the barrier layer 12'; similarly, the substrate layer 19; the ribbon 17 may be the same or different material as in the substrate 11'. A second alternative embodiment of the invention is shown in FIG. 7. In this embodiment, barrier layer 12" is discontinuously applied to substrate 11". The product layer 14" is initially applied in a different position on the barrier layer 12". The exact position of the product layer 14" on the barrier layer is not critical, so long as the product layer is disposed between layers or sheets of barrier material in the finished sampler.

Figure 6:
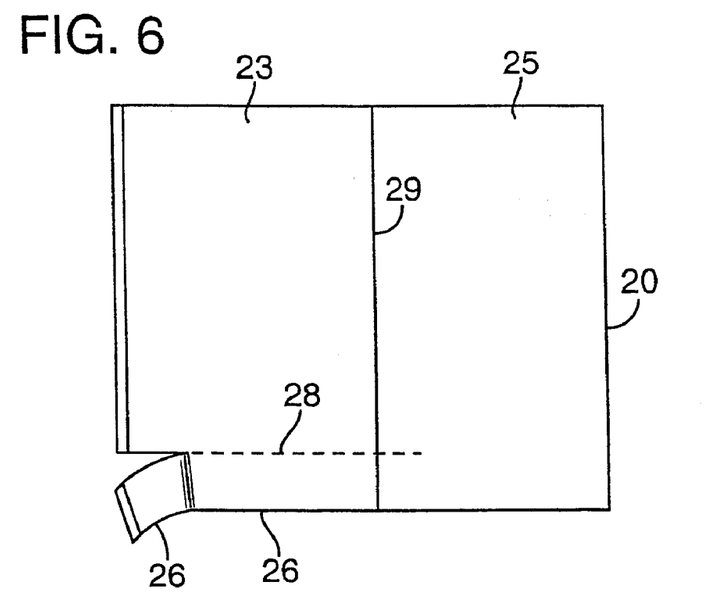
FIG. 6 is a plan view of the intermediate shown in FIG. 5, shown in a subsequent stage in the manufacturing process.

As shown in FIGS. 1 and 2, the sampler may be bound within a magazine along an edge, such as edge 20 or edge 21 (shown in FIG. 1), or by means of a separate attached hanger (not shown). Heretofore, if the sampler were bound within a magazine and a trim portion taken along a connecting edge, the removed trim portion would comprise a laminate of the barrier material and the substrate material. In contrast, in accordance with one embodiment of the present invention, the sampler has a non-barrier trimmable substrate edge tab, or protruding tab portion 22. By "non-barrier" is meant an edge portion that is not laminated to the barrier material. As shown in FIG. 5, the laminate of the barrier material with the substrate generally defines a barrier substrate region 23 and a non-barrier substrate region 25. To prepare the sampler, a portion of the barrier substrate region is removed along an edge 26 of the sampler, as shown in FIG. 6, preferably by cutting. As shown in FIG. 6, the cut line 28 should extend at least to the boundary 29 between the barrier substrate region 23 and the non-barrier substrate region 25. The cut line 28 may be made before or after a product layer has been applied, and before or after the product layer is covered with a layer of barrier material. The remaining portion of the edge 26 proximal to the removed portion of the barrier substrate material will comprise the non-barrier trimmable substrate edge tab portion 22, as shown in FIG. 1. If a trim is taken along the tab portion, the removed trim portion will comprise only the substrate material, and will not include any barrier material.

Preferably, the edge tab portion is homogeneous, that is, the edge tab portion is composed of a single substrate material. Such homogeneous construction allows for ready recycle or disposal of the trim portion. Thus, when binding the sampler into a magazine along edge 20, the magazine binder may take a trim from the tab portion 22 without removing barrier material with the removed trim portion.

In the alternative construction shown in FIG. 7, the barrier film 12" is not applied continuously over the substrate 11". In this embodiment, the non-barrier portions of the substrate may serve as a non-barrier trimmable edge portion. For example, a trim may be taken from edge 27. So long as the trim line 30 does not extend into the barrier film 12", the trim portion removed will be homogeneous, and the sampler thus may be provided with a non-barrier trimmable substrate edge portion.

As is conventional, the sampler may have printing across the non-barrier substrate region 25 (shown in FIG. 5). In addition, the barrier substrate region 23 may also be provided with printed graphics, as is not practical with currently produced fragrance samplers. Both the barrier substrate region 23 (shown in FIG. 5 on the inside of the sampler) and the non-barrier side 31 (shown in FIG. 1 on the outside of the sampler) thus may be provided with printed graphics. Printing may be applied in any conventional or otherwise suitable manner. The substrate and barrier layer may be otherwise modified or decorated as appropriate. For example, when the sampler edge is folded over the fold line 16 (as shown in FIG. 2), the non-barrier side 31 (shown in FIG. 1) of the substrate is partially exposed. The sampler may be provided with a cut, perforated, or scored pattern 33 to be folded over the product layer, the pattern 33 defining a patterned tab 34, whereby a user may pull away the tab 34 to expose the product layer 14.

Figure 8:
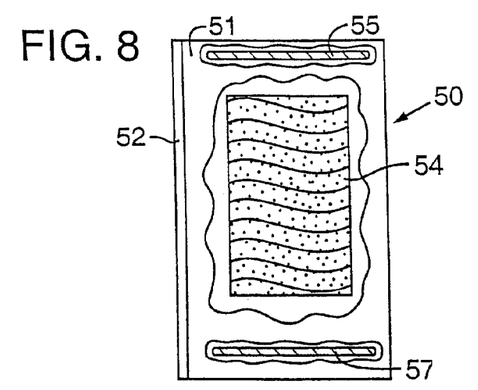
FIG. 8 is a plan view of a sampler in the form of a label, the label including two sheets of a substrate comprising a polymeric material having sufficient barrier properties so as not to require a separate barrier material, a portion of the top substrate film being cut-away.

In accordance with another embodiment of the invention, the sampler is in the form of a label, as illustrated by label 50 shown in FIG. 8. The label 50 includes sheets of a polymeric or other suitable barrier material 51, 52 having a gelatinoid product layer 54 disposed therebetween. The sheets 51, 52 may be of the same or different materials, so long as each serves a barrier function. No separate barrier or substrate layer thus is required, although a separate substrate (not shown) may be employed if desired for printability or other reasons. Resealable adhesive strips 55, 57 may be provided to seal the product layer 54 between the sheets 51, 52, although, when the product is provided in the form of a non-volatile gelatinoid product layer, such sealing of the label ordinarily is not required. The label of this embodiment of the invention readily may be distributed and handled, and may be resealed to allow for multiple uses.

Figure 9:
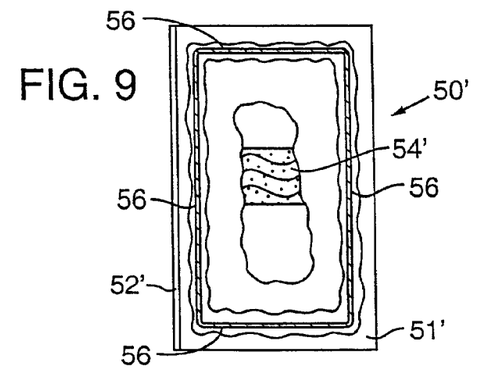
FIG. 9 is a plan view of an alternative embodiment of the sampler shown in FIG. 8.

Perimeter sealing ordinarily is not required of the samplers of the invention, although a perimeter seal may be employed if desired. Perimeter sealing may be employed where a longer shelf life is required of a sampler containing volatizing agents which may be added to increase the "lift" or strength of the fragrance. For example, as shown in FIG. 9, with respect to a sampler in the form of a label, the sampler 50' may include a gelatinoid product layer 54' contained within a space bounded by first and second sheets of barrier material 51', 52' and a wall defined by a thin layer of a perimeter adhesive 56, the adhesive 56 securing the first and second sheets of barrier material 51', 52' together and providing a perimeter seal for the product.

Figure 10:
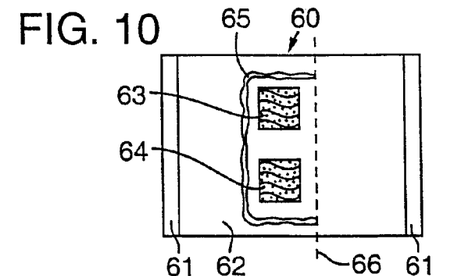
FIG. 10 is a plan view of another embodiment of the sampler of the invention, the sampler including two products and shown in an open position with the products exposed.

Similarly, a perimeter adhesive may be used when the sampler takes the form of a magazine insert. For example, FIG. 10 illustrates a sampler 60 that comprises a substrate 61, a layer of barrier material 62, and product layers 63, 64. The sampler 60 further includes a thin "wall" of perimeter adhesive 65. To seal the product layers within the sampler, the sampler is folded along fold line 66, thus sealing the product layers in a space bounded by the fold line 66, the wall of adhesive 65, and folded portions of the sheet of barrier material. In any embodiment of the invention wherein a perimeter adhesive is employed, any suitable adhesive may be used, and the choice of a particular adhesive will be within the level of skill in the art, in connection with the desired ultimate function of the adhesive. For example, various adhesives may be selected, the choice depending on whether the adhesive is to be used as a vapor seal to prevent loss of volatizing agents, as a physical barrier to prevent leakage, or as a tackifying agent to provide reclosability. The adhesive may comprise a heat sealable adhesive coating.

Conventional fragrance samplers employ adhesives to secure the fragrance microcapsules to the paper substrate. In accordance with preferred embodiments of the invention, the encapsulated fragrance or other product is provided in a gelatinoid form, i.e., a gelled or gel-like form. In this embodiment, the fragrance or other product contacts on a portion of the barrier material in a non-adhesive manner. By "non-adhesive" is meant that the gelatinoid product is in contact with the barrier layer or substrate in the absence of an adhesive layer that secures the product layer to the substrate or barrier layer.

The sampler of the invention may be used to deliver any suitable product. Preferably, the product is a microencapsulated product, and most preferably, the product is a microencapsulated fragrance. Any conventional fragrance microcapsules may be employed in conjunction with the invention, and many microencapsulation methods are known in the art. Most preferably, the microcapsules comprise a fragrant material contained within a space bounded by a wall material, the wall material being made from a highly cross-linked polymer, such as (but not restricted to) a polyester, a urea-based polymer, polyurea, polyamide, and so forth. Microcapsules having a gelatin-based wall material also may be employed. Preferably, the water content of the microcapsule portion is minimized prior to mixing with the vehicle, to thereby reduce the possibility that the rheological and aesthetic properties of the vehicle do not change upon evaporation of the water. The water content may be so minimized by any means suitable and known in the art, such as by filtering. The water content of the microcapsules preferably is reduced to a level below about 40%, more preferably, to a level below about 30%, and most preferably to a level in the range of zero to about 20%.

When the sampler is used to deliver a microencapsulated product or other product that is not itself gelatinoid in nature, the product should be dispersed or otherwise provided in a carrier vehicle, the product and vehicle thus defining the gelatinoid product. The carrier vehicle may comprise any material that is suitable for carrying the encapsulated product and forming a gelatinoid product layer which will not compromise the microcapsules, cause leakage of the microcapsule contents, nor accelerate diffusion thereof. Preferably, the carrier vehicle is a water-miscible material that is capable of being formulated to yield a gelatinoid compound or composition; more preferably, the carrier vehicle is a water-soluble material. Water solubility is desired to facilitate ease of incorporation of the fragrance microcapsules into the vehicle to form the product without the need for surfactants, emulsifying agents, homogenizers, or other ingredients to accommodate the water content of the microencapsulates. The carrier material further is preferably non-volatile, or is minimally volatile, to reduce the possibility that the rheological and aesthetic properties of the vehicle will change by evaporation of the carrier material. In accordance with highly preferred embodiments of the invention, the carrier vehicle is selected from among glycerin, propylene glycol, ethoxylated polyol esters, polyethylene glycol, polyethylene glycol monomethylether, and mixtures of the foregoing. The invention is not restricted to the foregoing, and indeed any suitable carrier vehicle may be chosen in connection with the invention.

The product carried in the sampler may comprise a mixture of microcapsules and the carrier vehicle. Preferably, the microcapsules are present in the carrier vehicle in an amount ranging from about 5% to about 55% by dry weight; more preferably, from about 15% to about 40% by dry weight; most preferably, from about 20% to about 35%. The balance of the product may comprise the carrier vehicle and any water present by virtue of the addition of the microcapsules. The microcapsules may be provided in the form of a non-flowing filter cake or otherwise as appropriate.

To assist in imparting a pleasant feel to the product, and to prevent migration of the product, the product may include a thickener. Any thickener that is effective in thickening the carrier vehicle may be employed. Suitable thickeners preferably are selected from among known thickeners, the exact choice depending in part upon the carrier vehicle chosen. When the carrier vehicle is glycerin, the thickener is preferably a polyacrylamide. Other suitable thickeners include PEMULEN TR-1 or TR-2, an acrylate/C10–30 alkyl acrylate cross polymer sold by B F Goodrich, other acrylic/acrylate copolymers, polymeric thickeners, polymeric emulsification, or other suitable thickeners. The thickener may be employed in any amount effective to thicken the product layer. Preferably, the thickener is present in the product layer composition in an amount ranging from about 0.05% to about 5% by weight; more preferably, from about 0.1% to about 2.0% by weight; and most preferably 0.2% to 1.0% by weight.

Alternatively, the desired viscosity may be achieved by the addition of a particulate filler, such as boron nitride or a modified starch. When a starch is used, the starch preferably is a hydrophobically modified starch selected from the DRY FLO starches (National Starch). If such a starch is used, no additional thickeners need be employed. Use of such fillers enhances product aesthetics by providing a drier, smoother, and silkier feel on the skin. The particulate nature of such fillers also helps to adsorb and contain any unencapsulated fragrance oil and prolong the shelf life of the sampler (particularly if a hydrophobic grade such as DRY-FLO PC or AF is used). Depending on the desired tactile properties the product layer may include an amount ranging from about 5% to about 25% of such starch; most preferably, if such starch is present, the product layer includes about 10% to about 18% starch.

The product layer should be sufficiently compatible with the barrier material so that the product layer will wet the barrier material. To assist in wetting, the product layer may include a surfactant. Any suitable surfactant may be employed in conjunction with the invention. Preferably, the surfactant is a non-ionic surfactant, for example octylphenoxypolyethoxyethanol or methyl/glucoside sesquistearate. The surfactant is an optional ingredient in the product layer composition. When used, the surfactant may be present in any amount effective to reduce the surface tension of the product layer composition. Preferably, the surfactant is present in the product in an amount ranging from about 0.05% to about 2% by weight, and more preferably, an amount ranging from about 0.1% to about 0.5% by weight.

Other ingredients may be added to the product as desired. For example, the product may include a preservative, an antimicrobial agent, an antioxidant, a volatizing agent, such as a volatile silicone, a colorant, and, in general, any other compatible material that imparts or enhances desirable properties. Such ingredients may be added in any suitable amounts. The microcapsule containing mixture need only be mixed conventionally to achieve homogeneity.

The fragrance or other product need not be provided in microencapsulated form, but may be provided in any other suitable gelatinoid form. For example, the fragrance or other product may be provided in the form of a non-microencapsulated emulsified product, which comprises an emulsion of fragrance oil in a suitable vehicle. The emulsified product should ideally be homogenized at a high speed and shear rate to achieve a dispersion of 0.10 to 5.0 micron oil droplets in the vehicle. A thickener may be added before or after emulsification to thereby stabilize the emulsion. The Theological and other properties of the emulsion then may be adjusted. Surfactants optionally may be employed to aid in stabilizing the emulsion, although surfactants are not generally desirable since they may promote diffusion of the fragrance from the sample layer. Such an emulsion of fragrance oil may have a shorter shelf life than an encapsulated fragrance product, but the emulsion will likely have the advantage of being less expensive than products that include a microencapsulated fragrance. In addition, the fragrance oil will likely impart a greater "lift" or initial burst of fragrance. In some embodiments of the invention, microcapsules may be used in conjunction with fragrance oils in the same product layer to thereby combine the benefits of initial lift and good shelf life. In other embodiments, the sampler may include two fragrance strips, for example, one being a microencapsulated fragrance and one being a non-encapsulated fragrance. For example, in the embodiment shown in FIG. 10, product layer 63 may be a non-encapsulated fragrance, and product layer 64 may be a microencapsulated fragrance.

Figure 11:
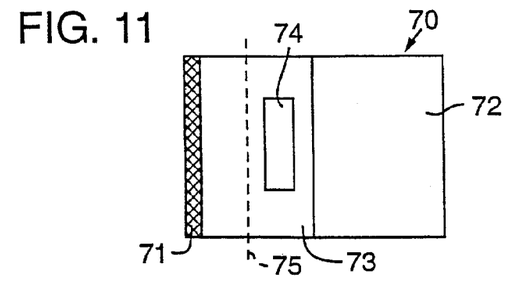
FIG. 11 is a plan view of another embodiment of the sampler of the invention, shown in open position with the product exposed.

In another embodiment of the invention, the sampler includes two fragrant products, one being a conventional microencapsulated fragrance that is disposed in an adhesive suspension and that is adhesively secured to the substrate or barrier layer, and the other being a gelatinoid product. For example, in the embodiment shown in FIG. 11, sampler 70 includes a conventional microencapsulated fragrance strip 71, which may be adhesively connected either to the substrate layer 72 or the barrier layer 73, but preferably to the substrate layer 72. The sampler 70 further includes a gelatinoid product layer 74, which preferably is a fragrant product and which may be the same as or different from the product in the microcapsule strip. The sample is folded over fold line 75 to form a folded pocket that is adhesively secured by the microcapsule strip 71. When the sampler is opened, the microcapsules in the strip 71 will rupture to release the microencapsulated fragrance in an initial "burst." The user then may sample the product in both the microcapsule strip 71 and in the gelatinoid product 74. The gelatinoid product 74 will allow for repeated use of the sampler over a longer period of time than could be attained with the microcapsule strip used alone. Various other combinations are possible.

In accordance with another preferred embodiment of the invention, the sampler includes fragrance oil provided in the form of a particulate product matrix containing the fragrance oil. Any compatible material may be employed to provide the particulate matrix, and preferred materials include amorphous silicon dioxide, such as AEROSIL (DeGussa), CABOSIL (Cabot), or modified corn starch (such as DRY FLO products available from National Starch). Preferably, the material used to provide the particulate matrix is a hydrophobic material. Alternately, the particulate product matrix is a polymeric material. One suitable material is POLYTRAP 6603 (Advanced Polymer Systems). The material of the matrix is provided in a quantity effective to contain most or all of the fragrance oil or other product. Generally, the particulate polymeric matrix acts as a sponge to contain and keep the emulsified ingredient suspended within the vehicle of the gelatinoid product layer. To provide a gelatinoid product layer, the fragrance oil or other product is mixed with the matrix, and this mixture is then emulsified or dispersed in the gelatinoid carrier vehicle. Use of such a particulate product matrix results in a stable pseudo-encapsulated product layer, and further provides a larger droplet size, which, in turn, allows for delivery of an increased "payload" of the oil product, as compared to emulsified fragrance oils.

The sampler of the invention is not limited to use in conjunction with fragrance products, but rather is useful in conjunction with any gelatinoid product or product that may be converted to a gelatinoid form for sampling. Thus, for example, the sampler may be used to deliver other materials, such as lotions, creams, and so forth. The sampler may also be used to deliver color cosmetic products such as lipsticks, rouges, blushes, foundations, and the like. The sampler may further be used to deliver non-cosmetic products, such as inks, dyes, and so forth. For example, in one embodiment of the invention, the sampler is a disposable fingerprint kit. In this embodiment, the sampler will deliver a gelatinoid fingerprint ink, which may include an encapsulated dye, dispersed pigment, or other colorant. Thus, it should be understood that the sampler of the invention may be used not only for marketing purposes, but also more generally as a delivery system for providing a variety of products for many uses.

The following examples illustrate the invention, but should not be construed as limiting in scope.

EXAMPLE 1

Fragrance Sampler

A sampler of laminar construction is made by applying a layer of polypropylene barrier material over a #2 clay-coated calendered sheet to form an intermediate laminate. Onto the barrier material is applied a gelatinoid product that comprises the following ingredients:

| | |
|---|---|
| Glycerin | 54.8% |
| Fragrance microcapsules | 29.7% |
| Water | 15. |
| PEMULEN TR-2 | 0.2% |

The intermediate laminate is folded over itself to seal the fragrance layer between the layers of polypropylene barrier material. Alternatively, a second layer of laminate is ribboned over the product layer.

EXAMPLE 2

Fragrance Sampler

A sampler is prepared in accordance with Example 1, except that the fragrance layer comprises an emulsion of fragrance oil in glycerin. The fragrance layer comprises the following ingredients:

| | |
|---|---|
| Fragrance oil | 30.0% |
| Glycerin | 69.0% |
| Polyacrylamide thickener | 1.0% |

EXAMPLE 3

A sampler is prepared in accordance with Example 1, except that the fragrance layer comprises a particulate absorption matrix having the following composition:

| | |
|---|---|
| Fragrance oil | 30.0% |
| AEROSIL R972 | 10.0% |
| Glycerin | 59. |
| Polyacrylamide thickener | 0.3% |

EXAMPLE 4

A sampler is prepared in accordance with Example 1, except that the fragrance layer comprises a particulate polymeric absorption matrix having the following composition:

| | |
|---|---|
| Fragrance Oil | 30.0% |
| POLYTRAP 6603 | 6.0% |
| Glycerin | 63.5 |
| Polyacrylamide thickener | 0.5% |

EXAMPLE 5

A sampler is prepared in accordance with Example 1, except that the fragrance oil contains a polymeric thickener and particulate matrix in the following water-miscible composition:

| | |
|---|---|
| Fragrance Oil | 30.0% |
| ETHOCEL S10 (Dow Corning) | 3.0% |
| AEROSIL R972 | 8.0% |
| Glycerin | 58.5% |
| Polyacrylamide thickener | 0.5% |

EXAMPLE 6

A sampler is prepared in accordance with Example 1, except that the fragrance layer comprises the following water-miscible composition:

| | |
|---|---|
| Microcapsule Cake | 60.0% |
| Glycerin | 39.5% |
| Polyacrylamide thickener | 0.5% |

EXAMPLE 7

A sampler is prepared in accordance with Example 1, except that the fragrance layer comprises the following water-miscible composition:

| | |
|---|---|
| Micracapsule "Cake" | 55.0% |
| Glycerin | 20.0% |
| Polyethylene Glycol | 24.5% |
| Polyacrylamide thickener | 0.5% |

With respect to polyethylene glycol, various molecular weights and grades are available, and the choice of a particular grade and use level will be within the level of skill in the art. Such choice largely will be dictated by desired tactile properties of the gelatinoid product layer, and/or by the method used to apply the product to the barrier substrate during manufacture.

EXAMPLE 8

A sampler is prepared in accordance with Example 1, except that the scent strip comprises the following water-immiscible composition:

| | |
|---|---|
| Microcapsules | 35.0% |
| DC 200 Fluid 10,000 cs. (Dow Corning) | 65.0% |

EXAMPLE 9

A sampler is prepared in accordance with Example 1, except that the scent strip comprises the following lower-viscosity water-immiscible composition:

| | |
|---|---|
| Microcapsules | 35.0% |
| DC 200 Fluid 1,000 cs. | 15.0% |
| DC 200 Fluid 10,000 cs. | 50.0% |

Examples 8 and 9 illustrate that the gelatinoid product layer may comprise a water-immiscible vehicle. Such vehicles may be more difficult to employ when the vehicle is used to carry a microencapsulated fragrance oil, inasmuch as the oil may be soluble in the vehicle and the microcapsules thus may become compromised. However, a water-immiscible vehicle may provide superior tactile properties, and thus may find use in connection with some microencapsulated applications. Moreover, a water-immiscible vehicle or solvent is preferred for some applications, such as color cosmetics, wherein solubility and diffusion of a fragrance oil are not at issue.

EXAMPLE 10

A sampler is prepared in accordance with Example 1, except that the fragrance strip has the following composition:

| | |
|---|---|
| AEROSIL 972 | 4.0% |
| Fragrance Oil | 12.5% |
| Microcapsule "cake" | 42.0% |
| Pclyacrylamide thickener | 0.5% |
| Glycerin | 41.0% |

In this Example, the fragrance sampler includes both a fragrance oil and microencapsulated fragrance. The sampler has a good initial "lift," and has a satisfactory shelf life.

EXAMPLE 11

A sampler is prepared in accordance with Example 1, except that the fragrance strip has the following composition:

| | |
|---|---|
| Glycerin | 41.0% |
| Fragrance Microcapsules | 38.0% |
| Modified Corn Starch | 21.0% |

In this Example, the starch imparts the fragrance strip with a smooth and silky feel on the skin.

EXAMPLE 12

A sampler is prepared in accordance with Example 1, except that two fragrance strips are employed. The first fragrance strip comprises a conventional fragrance strip that is adhesively secured to the substrate and that releases fragrance via rupture of microcapsules upon opening of the sampler. The second fragrance strip comprises the fragrance strip employed in conjunction with Example 1. Like the sampler of Example 10, this fragrance strip has a good initial "lift" and a satisfactory shelf life.

Thus, the foregoing general objects have been satisfied. The sampler of the invention is simple in construction, and may be quickly and inexpensively manufactured to allow for production of handouts, mailers, labels, inserts, and the like in a cost-effective manner not heretofore possible. In addition, the sample has an excellent barrier property, such that volatile components do not readily escape from the sampler. Moreover, the sampler has many versatile applications, and may be used, for example, to deliver products such as cosmetics and the like. In preferred embodiments of the invention, the sampler is provided in the form of a magazine insert having a non-barrier trimmable edge portion, this allowing for ready binding into a magazine and acceptability by magazine binders.

While particular embodiments of the invention have been shown, it will of course be understood that the invention is not limited thereto since modifications may be made by those skilled in the art, particularly in light of the foregoing teachings. It is, therefore, contemplated by the appended claims to cover any such modifications as incorporate those features which constitute the essential features of these improvements within the true spirit and scope of the invention.

What is claimed is:

1. A product sampler, comprising:
   a substrate;
   a first layer of a barrier material covering at least a portion of said substrate;
   a gelatinoid product layer covering at least a portion of said barrier layer and in contact with said barrier layer; and
   a second layer of a barrier material covering said product layer and in contact with said product layer,
   said gelatinoid product layer having been prepared by providing a non-volatile gelatinoid vehicle and providing a microencapaulated product in said vehicle, wherein said microencapsulated product comprises a product contained within a cavity defined by a wall material, said wall material being a material selected from the group consisting of urea resins and melamine resins.

2. A product sampler, comprising:
   a substrate;
   a first layer of a barrier material covering at least a portion of said substrate;
   a gelatinoid product layer covering at least a portion of said barrier layer and in contact with said barrier layer;
   a second layer of a barrier material covering said product layer and in contact with said product layer,
   said gelatinoid product layer having been prepared by providing a non-volatile gelatinoid vehicle and providing a product in said vehicle, whereby said product is carried in said vehicle; and
   a second product layer, said gelatinoid product layer being a microencapsulated product layer and said second product layer including a non-encapsulated fragrance oil.

3. A product sampler, comprising:
   a substrate;
   a first layer of a barrier material covering at least a portion of said substrate;
   a gelatinoid product layer covering at least a portion of said barrier layer and in contact with said barrier layer;
   a second layer of a barrier material covering said product layer and in contact with said product layer,
   said gelatinoid product layer having been prepared by providing a non-volatile gelatinoid vehicle and providing a product in said vehicle, whereby said product is carried in said vehicle; and
   a second product layer, said second product layer comprising a microencapsulated fragrance disposed in an adhesively secured relationship with respect to said sampler whereby at least a portion of the microcapsules in said second product layer rupture upon initial opening of said sampler.

4. A product sampler comprising:
   a first layer of barrier film;
   a gelatinoid product layer covering at least a portion of said first layer of barrier film and contacting said first layer of barrier film;
   a second layer of barrier film covering said gelatinoid product layer and contacting said gelatinoid product layer;
   said gelatinoid product layer having been prepared by providing a non-volatile gelatinoid vehicle and providing a product in said vehicle, whereby said product is carried in said vehicle; and a second product layer, said second product layer being a microencapsulated product layer;

said gelatinoid product layer including a non-encapsulated fragrance oil.

5. A product sampler, comprising:

a first layer of barrier film;

a gelatinoid product layer covering at least a portion of said first layer of barrier film and contacting said first layer of barrier film;

second layer of barrier film covering said gelatinoid product layer and contacting said gelatinoid product layer;

said gelatinoid product layer having been prepared by providing a non-volatile gelatinoid vehicle and providing a product in said vehicle, whereby said product is carried in said vehicle; and a second product layer, said second product layer comprising a microencapsulated fragrance disposed in an adhesively secured relationship with respect to said sampler whereby at least a portion of the microcapsules in said second product layer rupture upon initial opening of said sampler.

* * * * *